(12) United States Patent
Hultgren et al.

(10) Patent No.: US 9,757,141 B2
(45) Date of Patent: Sep. 12, 2017

(54) GUM TISSUE GUIDE, SYSTEMS AND METHODS OF PRODUCING AND UTILIZING THE SAME

(71) Applicants: Bruce Willard Hultgren, Victoria, MN (US); Michael Craig Marshall, Sheboygan, WI (US)

(72) Inventors: Bruce Willard Hultgren, Victoria, MN (US); Michael Craig Marshall, Sheboygan, WI (US)

(73) Assignee: Bruce W. Hultgren, Victoria, MN (US)

( * ) Notice: Subject to any disclaimer, the term of this patent is extended or adjusted under 35 U.S.C. 154(b) by 0 days.

(21) Appl. No.: 15/066,783

(22) Filed: Mar. 10, 2016

(65) Prior Publication Data

US 2016/0262783 A1    Sep. 15, 2016

Related U.S. Application Data

(60) Division of application No. 14/227,670, filed on Mar. 27, 2014, now Pat. No. 9,636,129, which is a
(Continued)

(51) Int. Cl.
*A61C 19/04* (2006.01)
*A61B 17/32* (2006.01)
(Continued)

(52) U.S. Cl.
CPC .............. *A61B 17/32* (2013.01); *A61B 5/0062* (2013.01); *A61B 5/742* (2013.01); *A61C 1/082* (2013.01);
(Continued)

(58) Field of Classification Search
CPC ......... A61C 1/082; A61C 1/084; A61C 1/085; A61C 1/087; A61C 1/10; A61C 1/14;
(Continued)

(56) References Cited

U.S. PATENT DOCUMENTS 3,521,355 A * 7/1970 Pearlman ................. A61C 7/14
433/3
4,138,814 A * 2/1979 Weitzman ............ A61C 19/063
433/215
(Continued)

OTHER PUBLICATIONS

Sarver DM, The face as determinant of treatment choice., vol. 38, University of Michigan Craniofacial Growth series, pp. 19-54, Ann Arbor, Michigan, 2001.
(Continued)

*Primary Examiner* — Yogesh Patel
(74) *Attorney, Agent, or Firm* — Mechant & Gould P.C.

(57) ABSTRACT

A method, device and system for modifying the gingival margin of a patient is disclosed. A method includes obtaining an electronic model of the dentition of a patient, determining an incision path along the gingival surface based on the electronic model, generating and fabricating a guide arrangement to assist in cutting the gingival surface of the patient, mounting the guide arrangement to the dentition of the patient, and cutting the gingival surface of the patient with the assistance of the guide arrangement. A guide arrangement includes a mounting portion and a template portion coupled to the mounting portion along the gingival surface of the guide arrangement and positioned to provide a desired incision path. A system includes a three dimensional scanner, a computer system and a fabricating device.

8 Claims, 14 Drawing Sheets

Related U.S. Application Data continuation of application No. 13/547,532, filed on Jul. 12, 2012, now Pat. No. 8,721,329.

(60) Provisional application No. 61/507,297, filed on Jul. 13, 2011.

(51) Int. Cl.

| | | |
|---|---|---|
| *A61C 19/00* | (2006.01) | |
| *A61C 3/02* | (2006.01) | |
| *A61C 9/00* | (2006.01) | |
| *A61C 1/08* | (2006.01) | |
| *A61C 3/00* | (2006.01) | |
| *A61C 19/055* | (2006.01) | |
| *A61B 5/00* | (2006.01) | |
| *A61C 1/00* | (2006.01) | |
| *A61C 13/00* | (2006.01) | |
| *A61B 17/00* | (2006.01) | |

(52) U.S. Cl.
CPC .................. *A61C 3/00* (2013.01); *A61C 3/02* (2013.01); *A61C 9/00* (2013.01); *A61C 19/00* (2013.01); *A61C 19/055* (2013.01); *A61B 5/0088* (2013.01); *A61B 2017/00526* (2013.01); *A61B 2017/320052* (2013.01); *A61C 1/0046* (2013.01); *A61C 9/004* (2013.01); *A61C 13/0019* (2013.01)

(58) Field of Classification Search
CPC .. A61C 3/00; A61C 3/02; A61B 17/32; A61B 5/0062; A61B 5/742
USPC ............................................. 433/72–76, 213
See application file for complete search history.

(56) References Cited

U.S. PATENT DOCUMENTS

| | | | |
|---|---|---|---|
| 4,657,508 A | 4/1987 | Dellinger | |
| 5,406,963 A * | 4/1995 | Adell .................. | A63B 71/085 |
| | | | 128/861 |
| 5,863,198 A | 1/1999 | Doyle | |
| 6,217,334 B1 | 4/2001 | Hultgren | |
| 7,494,338 B2 | 2/2009 | Durbin | |
| 7,574,025 B2 | 8/2009 | Feldman | |
| 8,376,745 B2 | 2/2013 | Stonisch | |
| 2002/0151769 A1* | 10/2002 | Kim ..................... | A61C 8/0089 |
| | | | 600/210 |
| 2003/0224310 A1 | 12/2003 | Andreiko | |
| 2006/0223021 A1 | 10/2006 | Cinader, Jr. et al. | |
| 2010/0203479 A1 | 8/2010 | Bulloch | |
| 2011/0100379 A1* | 5/2011 | Doctors ................. | A61F 5/566 |
| | | | 128/862 |

OTHER PUBLICATIONS

Tucker, Lloyd M., Framing your masterpiece: guidelines for treatment planning the ideal soft tissue framework, Interdisciplinary treatment planning : principles, design, implementation / editor, Michael Cohen, Chicago : Quintessence Pub., copyright 2008, 18 pages.

Sarver DM, Augmenting and Improving Esthetics through Surgical Intervention. In: McNamara JA Jr, Kapila SD, eds. Surgical Enhancement of Orthodontic Treatment. Monograph 47, Craniofacial Growth Series, Department of Orthodontics and Pediatric Dentistry and Center for Human Growth and Development, The University of Michigan, Ann Arbor, 2010, pp. 22-31.

Schabel et al., "Clinical photography vs. digital video clips for the assessment of smile esthetics," Angle Orthodontist, vol. 80, No. 4, 2010, pp. 678-684.

\* cited by examiner

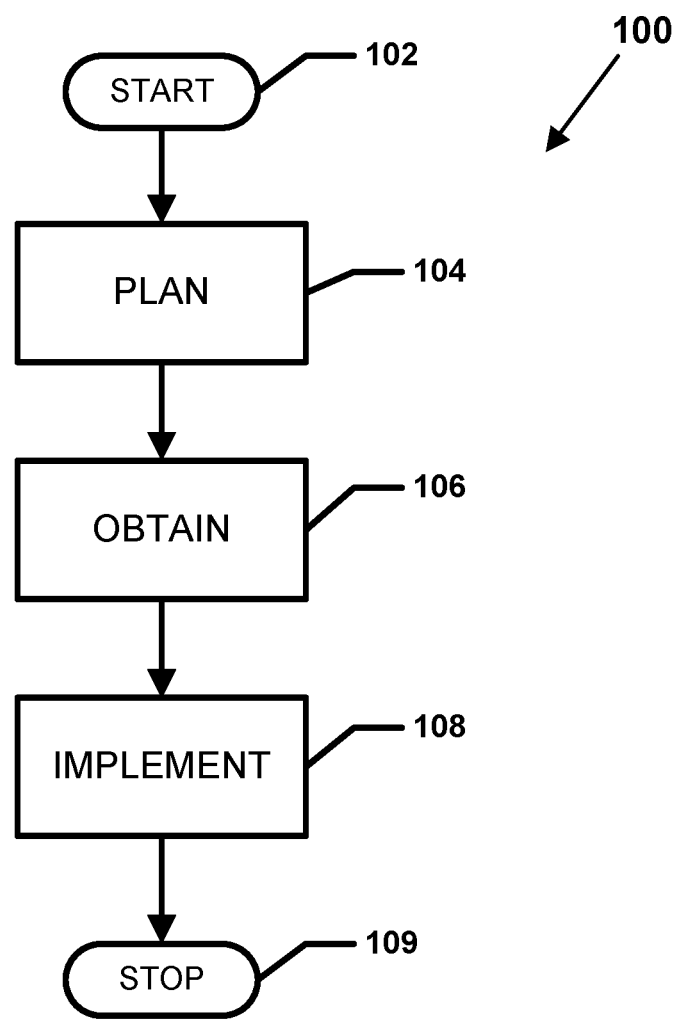

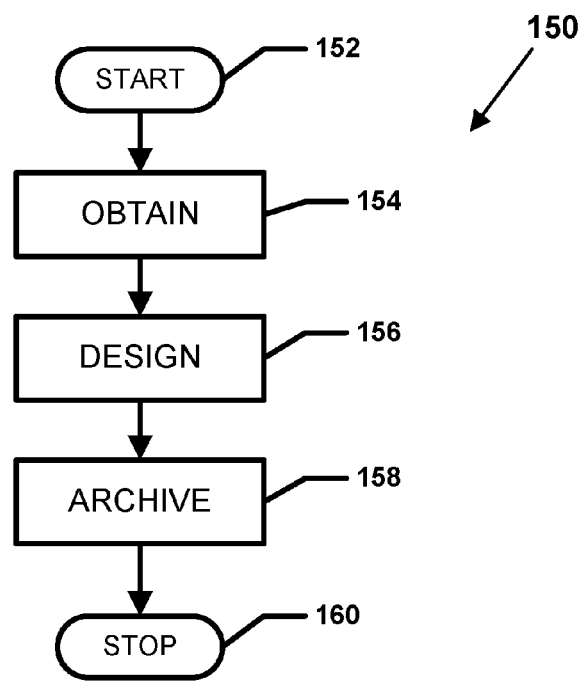
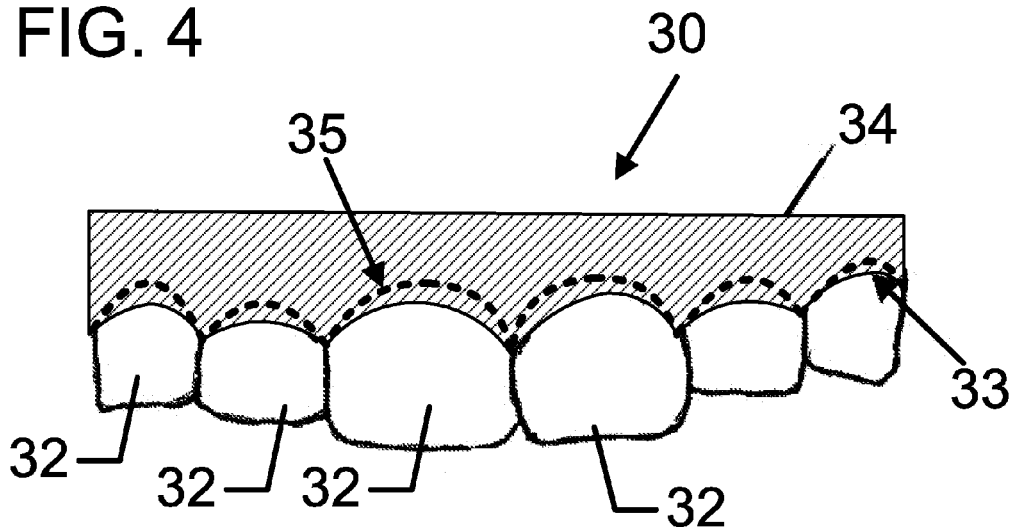

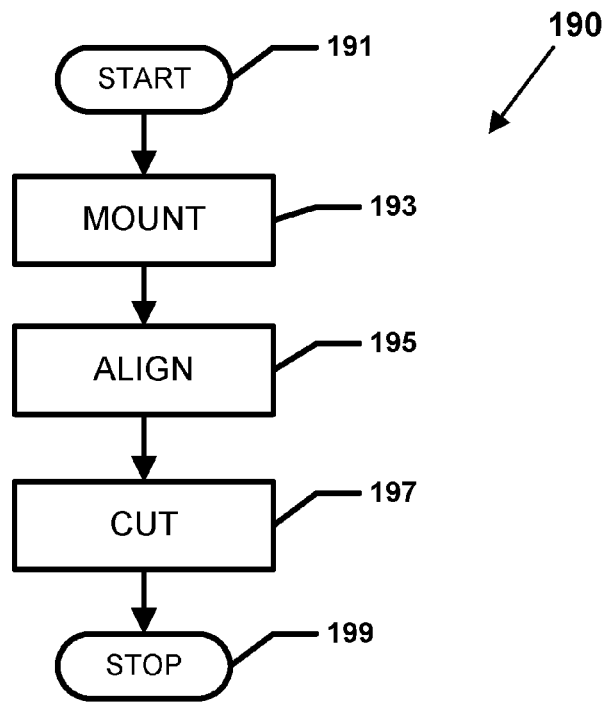
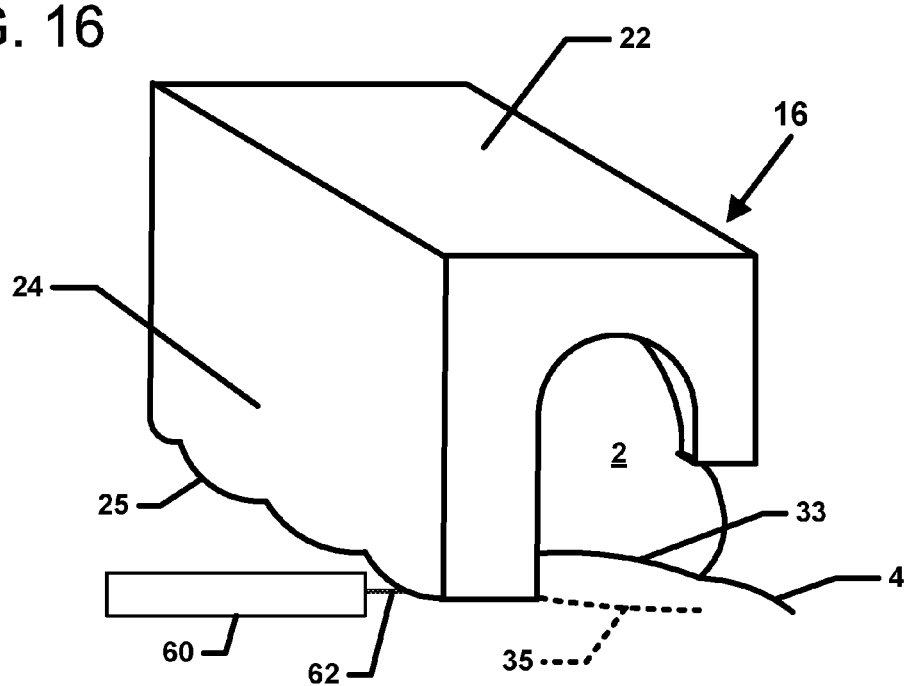

GUM TISSUE GUIDE, SYSTEMS AND METHODS OF PRODUCING AND UTILIZING THE SAME

CROSS REFERENCE TO RELATED APPLICATION

This application is a Divisional of U.S. application Ser. No. 14/227,670, U.S. Pat. No. 9,636,129, filed on Mar. 27, 2014, and issued on May 2, 2017, entitled GUM TISSUE GUIDE, SYSTEMS AND METHODS OF PRODUCING AND UTILIZING THE SAME, which is a Continuation of U.S. application Ser. No. 13/547,532, U.S. Pat. No. 8,721,329, filed on Jul. 12, 2012, issued on May 13, 2014, entitled GUM TISSUE GUIDE, SYSTEMS AND METHODS OF PRODUCING AND UTILIZING THE SAME, which claims priority to U.S. Provisional Patent Application Ser. No. 61/507,297, filed on Jul. 13, 2011, entitled GUM TISSUE GUIDE, SYSTEMS AND METHODS OF PRODUCING AND UTILIZING THE SAME, the disclosures of which are hereby incorporated by reference in their entireties. To the extent appropriate, a claim of priority is made to each of the above-disclosed applications.

TECHNICAL FIELD

The disclosure relates generally to a method, system, and device for manipulating the gingiva of a patient; and, more particularly, to a guide arrangement for use in cutting the gingival margin, and systems and methods for producing and utilizing the same.

BACKGROUND

Dental professionals routinely manipulate the gingiva of a patient for a variety reasons related to dental surgery, preventive maintenance, and aesthetics. For example, some dental patients can be unhappy with the post dental surgery aesthetics or natural aesthetics of their smile, including the presence of excess gingiva and/or unsymmetrical gingival margins and lines. Dental professionals sometimes address this concern by cutting the gingiva to remove excess gingiva and/or to improve the symmetry of the gingival lines, thereby increasing the general aesthetics of the patient's smile. The cutting of the gingiva is performed by hand (e.g., using a laser or a knife). Such techniques are inherently prone to human error and may not accurately reproduce a pre-operation plan incorporating the desired end result.

There arises a need in the art to provide a guide arrangement, and systems and methods for accurately allowing the manipulation of gingiva based on a pre-operation plan.

SUMMARY

The present disclosure provides for devices, systems, and methods for manipulating the gingiva of a patient; and, more particularly, a guide arrangement for use in cutting the gingival margin, and systems and methods for producing and utilizing the same.

In general, a dental professional develops a pre-operation plan for manipulating the gingiva of a patent to improve the aesthetics of the patient's smile. The plan includes obtaining an electronic model of at least part of a dentition of a patient, including a gingival surface. Determining an incision path along the gingival surface based at least partially on the electronic model image. Generating an electronic model of a guide arrangement including generating a mounting portion of the guide arrangement that is configured to fit over the dentition of the patient and generating a template portion of the guide arrangement that extends from the mounting portion towards the gingival surface of the patient. In a preferred embodiment, the template portion defines a guide edge along the incision path. And fabricating the guide arrangement based on the electronic model of the guide arrangement.

Following pre-operation planning and fabricating the guide arrangement, the guide arrangement can be mounted over the dentition of the patient and the gingival surface cut using the fabricated guide arrangement.

The guide arrangement used for cutting the gingival of a patient can include a mounting portion configured to couple to the dentition of the patient and a template portion coupled to the mounting portion along the gingival surface of the guide arrangement and positioned to provide a desired incision path. In a preferred embodiment, the guide arrangement further comprises a safety lip along the template portion of the guide arrangement to limit the proximity of a cutting tool to the gingival surface, prevent accidental cutting of the guide arrangement and improve the movement of a cutting tool across the template portion of the guide arrangement.

A system for fabricating the guide arrangement can include a three-dimensional scanner; a computing system; and a fabricating device. The scanner digitizes the dentition of the patient to generate electronic model images of the patient's teeth. The computing system enables display, manipulation, storage, and transmission of the electronic model images. The computing system also enables the user to design an electronic model of an guide arrangement configured to aid in manipulating the gingiva of a patient. The fabrication device enables fabrication of the alignment device based on the electronic model.

While the disclosure will be described with respect to preferred embodiment configurations and with respect to particular devices used therein, it will be understood that the disclosure is not to be construed as limited in any manner by either such configuration or components described herein. Also, while the particular types of scanning devices, computing devices, and fabrication devices used in the preferred embodiment are described herein, it will be understood that such particular components are not to be construed in a limiting manner. Instead, the functionality of those devices should be appreciated. These and other variations of the disclosure will become apparent to those skilled in the art upon a more detailed description of the disclosure.

The advantages and features which characterize the disclosure are pointed out with particularity in the claims annexed hereto and forming a part hereof. For a better understanding of the disclosure, however, reference should be had to the drawing which forms a part hereof and to the accompanying descriptive matter, in which there is illustrated and described a preferred embodiment of the disclosure.

BRIEF DESCRIPTION OF THE DRAWINGS

Referring to the drawing, wherein like numerals represent like parts throughout the several views:

FIG. 2 is a flowchart illustrating an operational flow of an example treatment process in accordance with the principles of the present disclosure;

FIG. 3 is a flowchart illustrating an operational flow of an example plan process by which a treatment plan is formed for a patient;

FIG. 4 shows an example incision path displayed over a dentition model in accordance with aspects of the disclosure;

FIG. 15 is a flowchart illustrating an operational flow for surgical process using a fabricated guide arrangement;

FIG. 16 shows a fabricated guide arrangement positioned over one or more teeth of the patient and a cutting tool aligned with a guide edge of the guide arrangement;

DETAILED DESCRIPTION

The present disclosure provides for methods, devices, and systems for manipulating the gingiva of a patient; and, more particularly, a guide arrangement for use in cutting the gingival margin, and systems and methods for producing and utilizing the same.

In general, a dental professional can plan and implement a course of treatment to manipulate the gingiva of a patient to produce a more aesthetically pleasing gingival line. In accordance with aspects of the disclosure, the dental professional may utilize one or more guide arrangements to aid the dental professional in cutting the gingival in accordance with the treatment plan. In accordance with aspects of the disclosure, a suitable guide arrangement may be designed and fabricated using one or more electronic models of the dentition of the patient.

Figure 1A:
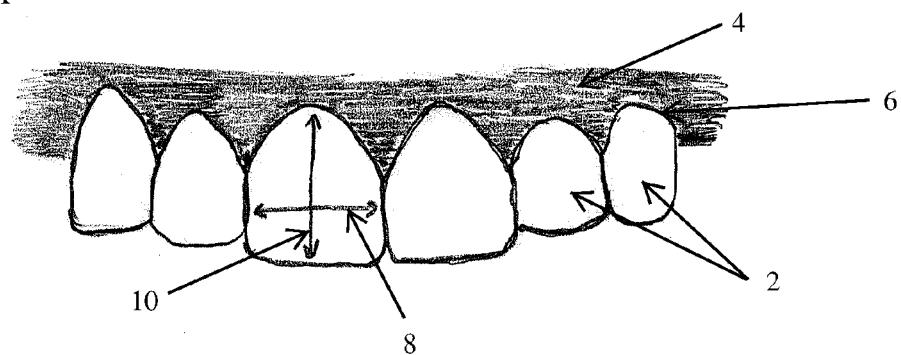
FIG. 1A illustrates a general frontal overview of a portion of a dentition of a patient including central incisors, lateral incisors, and canines in accordance with aspects of the disclosure.
Figure 1B:
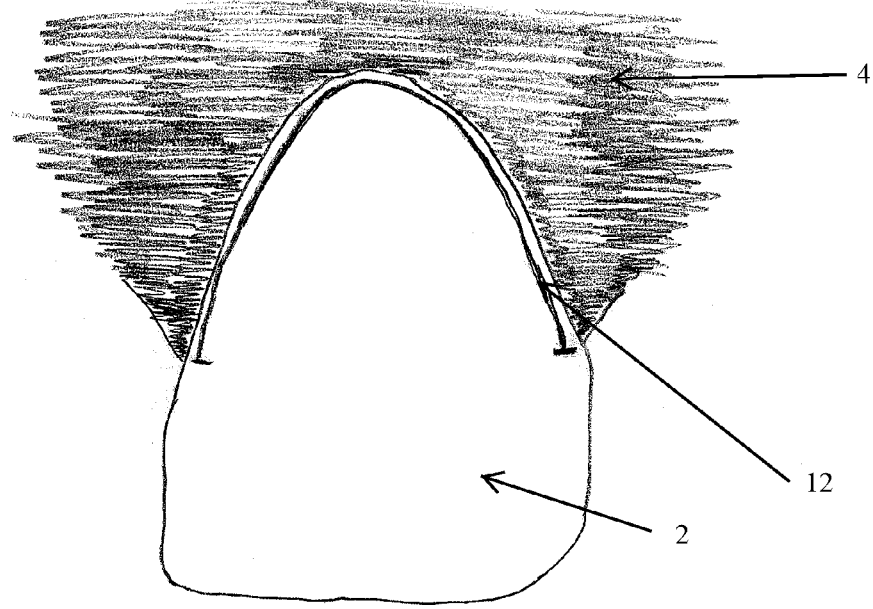
FIG. 1B is an enlarged view of one of the teeth of FIG. 1A.

FIGS. 1A and 1B generally shows a portion of a dentition of a patient. The illustrated portion includes six teeth 2, including the central incisors, lateral incisors, and canines. The roots of the teeth 2 are covered by gingiva 4. The crowns of the teeth 2 emerge from the gingiva 4 at a gingival margin 12. Each tooth crown has a maximum height 10 (e.g., the vertical distance between the gingiva line 12 to an occlusal end of tooth 2) and a maximum width 8 across the tooth 2. The gingival margin 12 defines the boundary between the teeth 2 and the gingiva 4 of a patient.

FIG. 2 is a flowchart illustrating an operational flow for a treatment process 100 in accordance with aspects of the disclosure. The treatment process 100 is implemented by the dental professional to plan and implement a course of treatment to modify the gingiva 4 of a patient. Referring to FIG. 2, the treatment process 100 begins at a start module 102, implements any suitable initial procedures, and proceeds to a plan operation 104.

In the plan operation 104, a dental professional creates a treatment plan for modifying the gingiva 4 of a patient. The treatment plan includes determining an incision path (e.g., see FIG. 4) along which the dental professional will cut the gingiva 4 during surgery. A dental professional plans a course of treatment for a patient by analyzing the dentition of the patient and determining a preferred gingival margin. In determining a preferred gingival margin, a dental professional may consider the symmetry of the gingival margin 12 for each tooth 2 and the symmetry of the gingival margin 12 between adjacent teeth 2.

Other example factors in determining a preferred gingival margin 12 include a target height 10 of each tooth 2, a target width 8 of each tooth 2, a preferred height 10 to width 8 ratio of each tooth 2, a current location of the gingival margin 12, a location of a gingival zenith, and the general aesthetics desired by the patient. Further details regarding such treatment planning can be found, e.g., in Tucker, L M, Framing Your Masterpiece: Guidelines for Treatment Planning the Ideal Soft Tissue Framework.).

In an obtain operation 106, a dental professional can obtain a guide arrangement (e.g., see guide arrangement 16 of FIG. 7) to aid the dental professional in cutting along the incision path. The guide arrangement is configured to be positioned over one or more teeth 2 of the patient and to provide a clear indication of the incision path along the gingiva 4 of the patient. Additional details pertaining to suitable guide arrangements, as well as the design and manufacture thereof, are provided herein.

In an implement operation 108, the dental professional mounts the obtained guide arrangement onto one or more teeth of the patient and cuts the patient's gingiva along a guide edge provided by the guide arrangement. The original gingival margin is hidden from view beneath the guide arrangement during the initial incisions. In one embodiment, the guide arrangement is similar to a mouth guard, and may cover the entire upper or lower teeth 2 of a patient. After cutting along the incision path, the dental professional may detach the guide arrangement and removes soft tissue located between the original gingival margin and the incision.

The treatment process 100 performs any appropriate concluding procedures and ends at a stop module 109.

FIG. 3 is a flowchart illustrating an operational flow of one example plan process 150 by which the dental professional creates a treatment plan. For example, the plan process 150 may be used to implement the plan operation 104 of FIG. 1. FIG. 4 shows an example treatment plan having an incision path 35 resulting from the plan process 150. The plan process 150 begins at a start module 152, performs any appropriate initialization procedures, and proceeds to an obtain operation 154.

In an obtain operation 154, the dental professional obtains one or more electronic models 30 (FIG. 4) of the dentition of the patient. Each electronic model 30 includes representations of one or more teeth 32 emerging from a gingival surface 34 at a gingival margin 33. In some embodiments, the electronic model 30 represents the teeth 32 located on one of the mandible and the maxilla of the patient. In other embodiments, however, the electronic model 30 represents the teeth 32 located on both the mandible and the maxilla. In still other embodiments, the electronic model 30 represents the teeth 32 of only the portion of the dentition for which gingival modification is planned.

In certain embodiments, the electronic model 30 is formed from a polygonal mesh. In one example embodiment, the electronic model 30 is formed from a triangular polygonal mesh. In other embodiments, however, other types of electronic models 30, such as voxel-based models, can be utilized. In some implementations, the dental professional may retrieve one or more electronic models 30 from memory on a local or remote computer. In other implementations, the dental professional may receive one or more electronic models 30 from a third party (e.g., via email, via network connection, via storage hardware, etc.).

In still other implementations, the dental professional may generate the electronic models 30 from positional data obtained, directly or indirectly, from the patient. For example, in some implementations, the obtain operation 154 acquires spatial data of the patient's dentition by scanning a dental cast of the patient's dentition and generating the electronic model 30 based on the obtained spatial data. In other implementations, the obtain operation 154 acquires the spatial data by intra-orally scanning the actual dentition of the patient. In still other implementations, the obtain operation 154 scans a negative impression taken of the patient's dentition.

Still referring to FIG. 3, in a design operation 156, the dental professional can define an incision path 35 (FIG. 4) along the gingival surface 34 based at least partially on the obtained electronic model 30. In some embodiments, the dental professional defines the incision path 35 by displaying the electronic model 30 of the dentition on a display device and mapping a desired gingival contour over the displayed electronic model through a user interface of the display device (e.g., see FIG. 4).

In some implementations, the dental professional determines a desired gingival contour based on a variety of factors, including the target height 10 (FIG. 1A) of each tooth 2, the target width 8 (FIG. 1A) of each tooth 2, a preferred height 10 to width 8 ratio, the location of the actual gingival margin (e.g., 12 of FIG. 1B), the location of the gingival zenith, and the general aesthetics desired by the patient. In certain implementations, the identification of an appropriate incision path 35 can be supplemented by software that automatically identifies the gingival margin 33 between the gingiva 34 and the teeth 32.

In an optional archive operation 158, the dental professional may store the treatment plan in memory (e.g., of a local computer, of a remote computer, etc.). For example, in some implementations, the dental professional may store the electronic model 30 of the dentition and a digital representation of the incision path 35.

The example plan process 150 performs any appropriate completion procedures and ends at a stop module 160.

Figure 5:
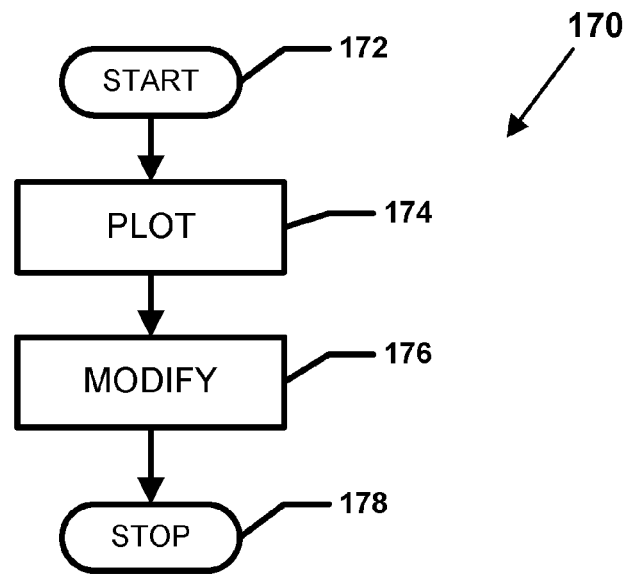
FIG. 5 is a flowchart illustrating an operational flow of one example design process by which the dental professional creates an incision path along which the dental professional will cut during surgery.
Figure 6:
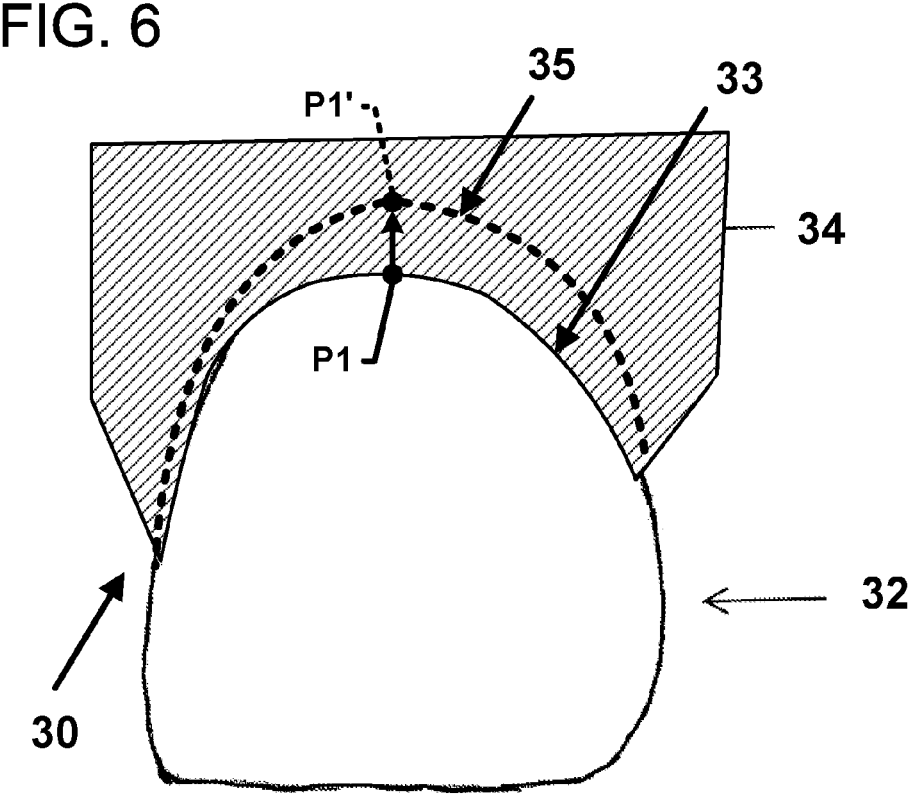
FIG. 6 is an enlarged view of a portion of the dentition model of FIG. 4 in which control points are moveable to adjust a contour of the incision path.

FIG. 5 is a flowchart illustrating an operational flow of one example design process 170 by which the dental professional creates an incision path 35 along which the dental professional will cut during surgery. For example, the design process 170 may be used to implement the design operation 156 of FIG. 3. FIG. 6 shows a portion of the example electronic model 30 including a tooth 32 emerging from a gingiva 34 at a gingival margin 33. FIG. 6 also shows an incision path 35 over the electronic model 30. The design process 170 begins at a start module 172, performs any appropriate initialization procedures, and proceeds to a plot operation 174.

The plot operation 174 provides one or more control points that define the incision path 35. In some implementations, the plot operation 174 initially provides the control points along the gingival margin 33. For example, a representative point P1 is shown on the gingival margin 33 in FIG. 6. In other implementations, a user may position the control points manually using a graphic user interface in the plot operation 174. In still other implementations, the plot operation 174 may automatically position the control points along a suggested incision path 35 based programmed factors. For example, in one implementation, the plot operation 174 may suggest control point positions based on a predetermined offset from the gingival margin 33.

A modify operation 176 adjusts the location of the control points to revise the incision path 35. In some implementations, a user may drag or otherwise relocate one or more control points manually using a graphic user interface. In other implementations, a user may change parameters (e.g., an offset from the gingival margin 33) being used by the computer to suggest control point locations. In the example shown in FIG. 6, the control point P1 on the gingival margin 33 is shown being moved to a new location (designated at P1'). Moving the control point P1 shifts the lines/curves connecting the control points.

The design process 170 performs any appropriate completion procedures and ends at a stop module 178.

Figure 7:
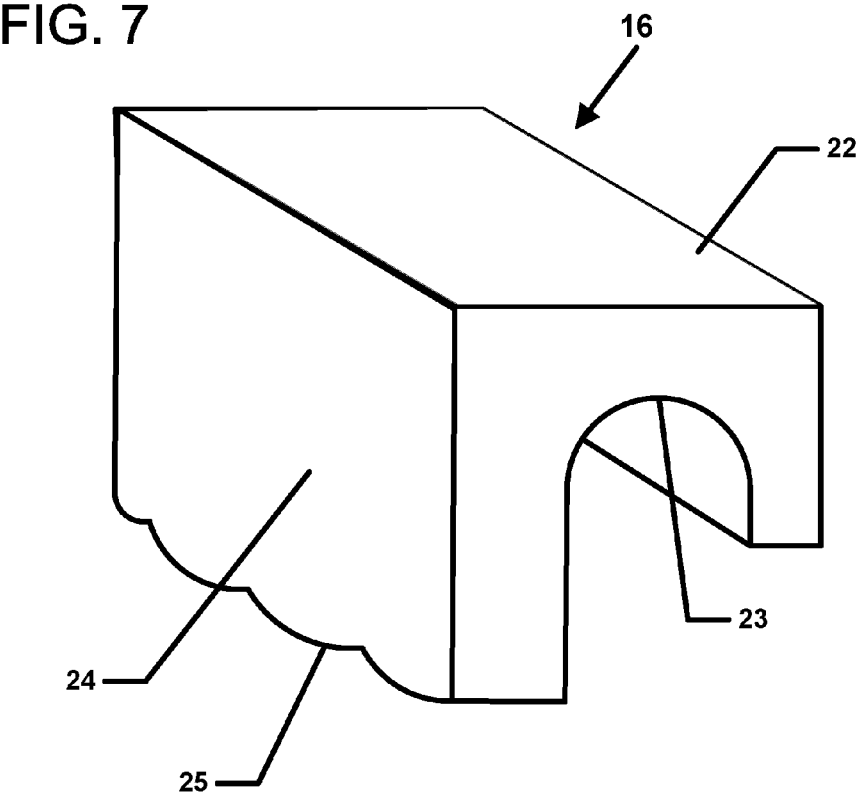
FIG. 7 is a schematic view of one example implementation of a guide arrangement suitable for use in guiding a dental professional in cutting along a planned incision path in accordance with aspects of the present disclosure.

FIG. 7 is a schematic view of one example implementation of a guide arrangement 16 suitable for use in guiding a dental professional in cutting along a planned incision path. The guide arrangement 16 includes a mounting portion 22 and a template portion 24 that is coupled to the mounting portion 22. The mounting portion 22 defines an interface 23 that is configured to seat on one or more teeth of the patient. The template portion 24 is designed to provide a guide edge 25 that follows the designed incision path. The guide edge 25 also provides a surface along which the cutting tool may be positioned and moved (e.g., slid) to cut the gingiva of the patient during treatment.

Figure 8:
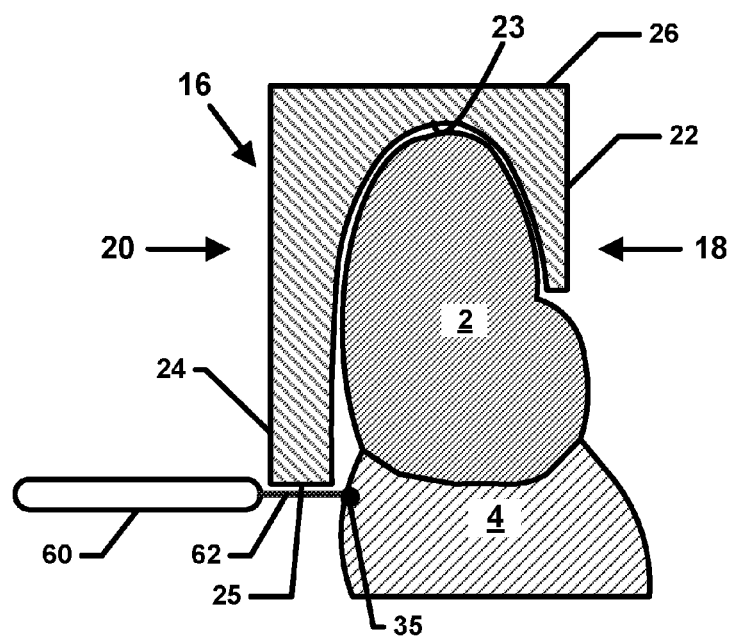
FIG. 8 is a cross-sectional view of the example guide arrangement of FIG. 7 positioned over a tooth of a patient with a buccal side of the tooth on the left and the lingual side of the tooth on the right.

FIG. 8 is a cross-sectional view of an example guide arrangement 16 positioned over a tooth 2 of a patient with a buccal side 20 of the tooth 2 on the left and the lingual side 18 of the tooth 2 on the right. The interface region 23 seats on an occlusal surface of the tooth 2. The interface region 23 is customized to the patient so that the guide arrangement 16 will mount to the dentition in only one orientation so as to indicate where on the gingiva 4 an incision path 35 is planned.

The template portion 24 of the guide arrangement extends over the buccal side 20 of the tooth 2 towards the gingiva 4. A guide edge 25 aligns with the designed incision path 35 at the gingiva 4. The guide edge 25 aligns a cutting section 62 of a cutting tool 60 with the incision path 35. In certain implementations, the guide edge 25 of the template portion 24 represents the contour of the patient's gingival margin post treatment. During the procedure, the original gingival margin is hidden from view beneath the guide arrangement 16. After cutting, soft tissue located between the original gingival margin and the incision may be removed.

In some implementations, the guide arrangement 16 at least partially covers the buccal, occlusal and lingual surfaces of the tooth 2. In other implementations, the guide arrangement 16 may contact only the buccal surface 20 and the occlusal surface of the tooth 2. In still other implementations, the guide arrangement 16 may contact only the buccal surface 20 of the tooth 2. The extent to which the guide arrangement 16 covers the tooth 2 depends on how the dental professional attaches the guide arrangement 16 to the tooth 2 (e.g., adhesive, friction, or the patient's bite).

The dental professional can mount the guide arrangement 16 to the patient's dentition in a variety of ways. In some implementations, the interface region 23 of the guide arrangement 16 is sufficiently offset from the tooth 2 to provide space for adhesive. In other implementations, the interface region 23 of the guide arrangement 16 is sufficiently tight to the tooth 2 to provide a friction fit against the tooth 2. In still other implementations, an occlusal surface 26 of the guide arrangement 16 may be provided at an appropriate height to allow a patient to bite down on the guide arrangement 16 to hold the guide in position.

The guide arrangement 16 may be designed to cover anywhere from two to sixteen teeth 2 depending on the preferences of the dental professional, the number of teeth 2 where gingiva 4 will be removed, and the method in which the guide arrangement 16 will be attached to the teeth 2. For example, the guide arrangement 16 may cover fewer teeth when using an adhesive for attachment than when using a friction fit.

Figure 9:
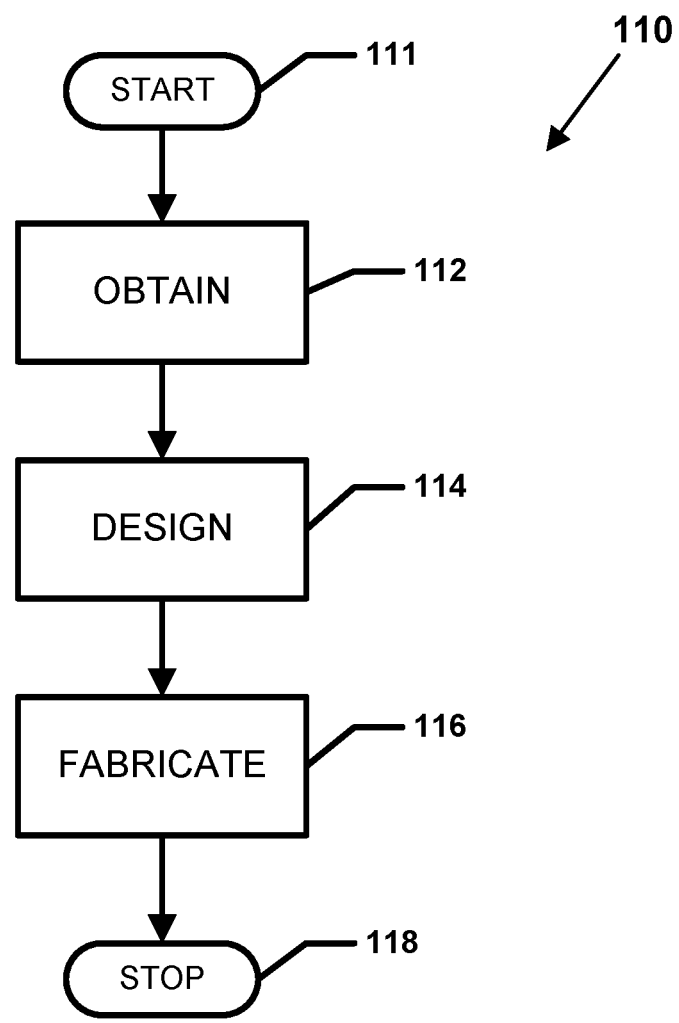
FIG. 9 is a flowchart illustrating an operational flow for an example manufacturing process by which a guide arrangement may be produced.
Figure 10:
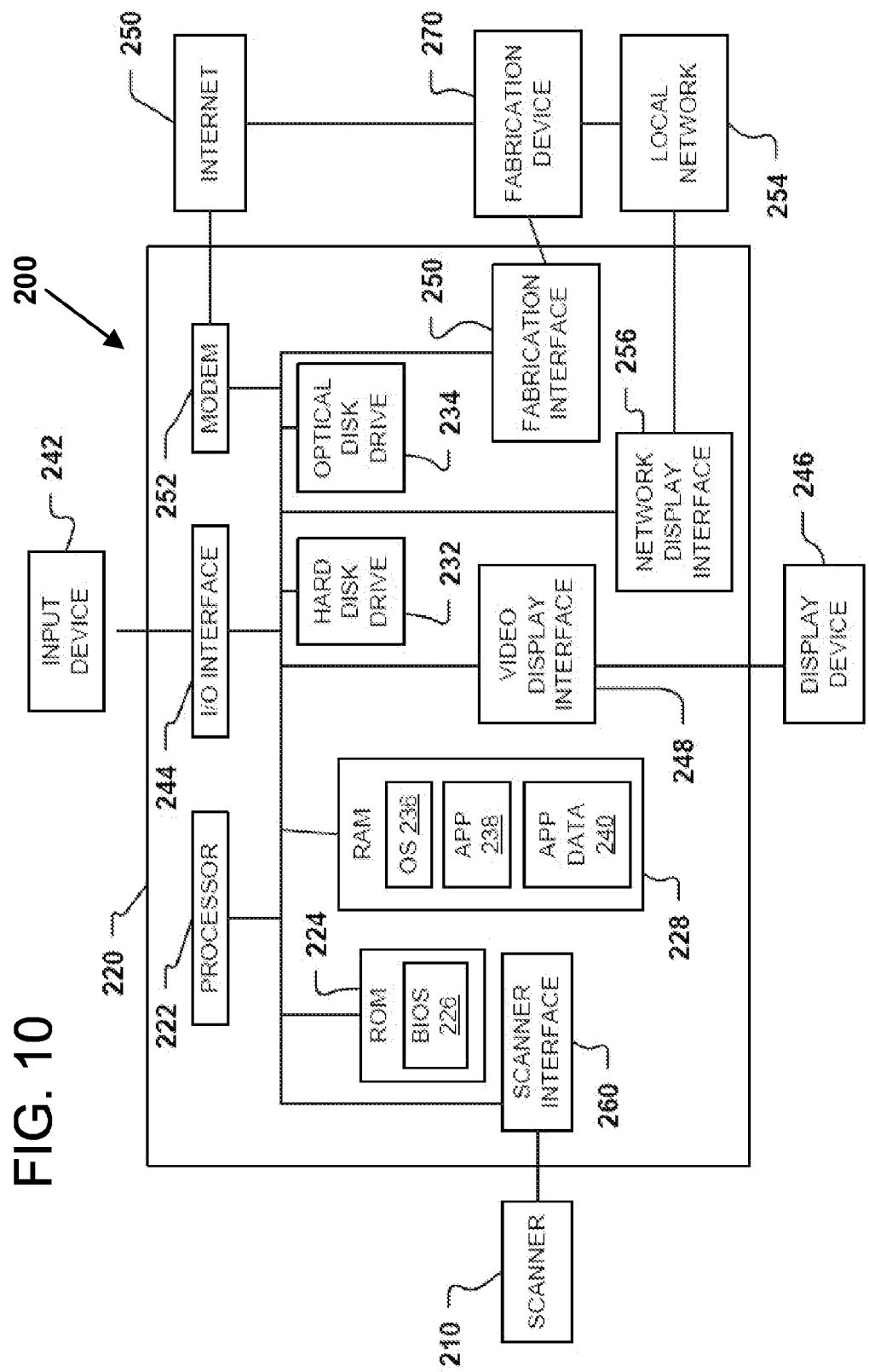
FIG. 10 is a schematic block diagram of an example computing system on which at least portions of the manufacturing process of FIG. 9 may be implemented.

Referring now to FIGS. 9-14, one or more guide arrangements 16 may be custom designed and manufactured for each patient. FIG. 9 is a flowchart illustrating an operational flow for an example manufacturing process 110 by which a guide arrangement 16 may be produced. FIG. 10 is a schematic block diagram of an example computing system 200 on which at least portions of the manufacturing process 110 may be implemented. The manufacturing process 110 begins at a start module 111, performs any appropriate initialization procedures, and proceeds to an obtain module 112.

The obtain module 112 acquires a treatment plan for a patient. The treatment plan includes an incision path along which a dental professional will cut into the gingiva 4 of a patient during a surgical procedure. In certain implementations, the obtain module 112 receives an electronic model 30 of the patient's dentition including the incision path 35 mapped over the gingival portion 3 of the electronic model 30. In some implementations, the obtain module 112 retrieves the treatment plan from electronic memory of a local or remote computer. In other implementations, the obtain module 112 obtains the treatment plan from an email or from storage hardware. In still other implementations, the obtain module 112 obtains positional data for the incision path separate from the electronic model 30.

A design operation 114 generates an electronic model 300 (FIG. 12) of a guide arrangement 16 based, at least in part, on the electronic model 30 of the dentition. In some implementations, the design operation 114 includes generating a mounting portion 322 of the guide arrangement model 300 that is configured to support the guide arrangement 16 when the guide arrangement 16 is positioned in the patient's mouth. For example, generating the mounting portion 322 includes generating an interface region 323 of the guide model 300 to provide proper fit and placement of the guide arrangement 16 based on interactions with the teeth 32 of the dentition model 30. The design operation 114 also includes generating a template portion 24 of the guide arrangement model 300 to extend towards the gingiva 4 of the patient to define a guide edge 25 along the incision path 35.

A fabricate operation 116 produces the guide arrangement 16 in accordance with the guide arrangement model 300. In some implementations, the fabricate operation 116 sends the guide model 300 or spatial data pertaining thereto to a third party for fabrication. In other implementations, the fabricate operation 116 sends the guide model 300 or spatial data pertaining thereto to a fabrication device to produce the guide arrangement 16. In some implementations, the fabrication device mills the guide arrangement 16 from a biocompatible material, such as dental wax or metal. In other implementations, the fabrication device prints the guide arrangement 16 from a biocompatible using a rapid prototyping machine. In still other implementations, the fabricate operation 116 produces a pattern from which the guide arrangement 16 may be cast.

The manufacturing process 110 performs any appropriate completion procedures and ends at a stop module 118.

As shown in FIG. 10, an example design and production system 200 on which example processes of the present disclosure can be executed includes a computing system 220. In some implementations, the computing system 220 is configured to implement the obtain operation 112 and design operation 114 of the manufacturing process 110 of FIG. 9. For example, the system is configured to enable display, manipulation, storage, and transmission of electronic models and/or spatial data. The system also can be configured to enable a user to manipulate the electronic model or portions thereof to plan a desired gingival contour of the teeth.

In some implementations, the computing system 220 also is configured implement the fabricate operation 116 of the manufacturing process 110 of FIG. 9. For example, in certain implementations, the computing system 220 is coupled to a fabrication device 270 that is capable of producing (e.g., print or milling) objects based on electronic models generated by the computing system 220. In other implementations, the computing system 220 may be coupled to a scanner 210 or other source of positional information.

One example implementation of the computing system 220 includes a processor unit 222, read only memory (ROM) 224, random access memory (RAM) 228, and a system bus 230 that couples various system components including the RAM 228 to the processor unit 222. The system bus 230 may be any of several types of bus structures including a memory bus or memory controller, a peripheral bus and a local bus using any of a variety of bus architectures. A basic input/output system 226 (BIOS) is stored in ROM 224. The BIOS 226 contains basic routines that help transfer information between elements within the computing system 220.

The computing system 220 further includes a hard disk drive 232 for reading from and writing to a hard disk, a magnetic disk drive (not shown) for reading from or writing to a removable magnetic disk, and an optical disk drive 234 for reading from or writing to a removable optical disk, such as a CD-ROM, DVD, or other type of optical media. The hard disk drive 232, magnetic disk drive, and optical disk drive 234 can be connected to the system bus 230 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the computing system 220.

Although the exemplary environment described herein employs a hard disk drive 232, a removable magnetic disk, and removable optical disk drive 234, other types of computer-readable media capable of storing data can be used in the exemplary system. Examples of these other types of computer-readable mediums that can be used in the exemplary operating environment include magnetic cassettes, flash memory cards, digital video disks, and Bernoulli cartridges. All of these physical devices are examples of computer-readable storage devices.

A number of program modules may be stored on the ROM 224, RAM 228, hard disk drive 232, magnetic disk drive, or optical disk drive 234, including an operating system 236, one or more application programs 238, other program modules, and program (e.g., application) data 240.

A user may enter commands and information into the computing system 220 through input devices 242, such as a keyboard, touch screen, and/or mouse (or other pointing device). Examples of other input devices may include a microphone, joystick, game pad, satellite dish, and document scanner. These and other input devices are often connected to the processor unit 222 through an I/O port interface 244 that is coupled to the system bus 230. Nevertheless, these input devices 242 also may be connected by other interfaces, such as a parallel port, game port, or a universal serial bus (USB). A monitor 246 or other type of display device is also connected to the system bus 230 via an interface, such as a video adapter 248. In addition to the display device 246, computing systems typically include other peripheral output devices (not shown), such as speakers and document printers.

The computing system 220 may operate in a networked environment using logical connections to one or more remote computers. Examples of remote computers include personal computers, servers, routers, network PC's, peer devices and other common network nodes, and typically include many or all of the elements described above relative to the computing system 220. In certain embodiments, the network connections can include a local area network (LAN) or a wide area network (WAN). Such networking environments are commonplace in offices, enterprise-wide computer networks, intranets, and the Internet 250.

When used in a WAN networking environment, the computing system 220 typically includes a modem 252 or other means for establishing communications over the wide area network, such as the Internet 250. The modem 252, which may be internal or external, can be connected to the system bus 230 via the I/O port interface 244. When used in a LAN networking environment, the computing system 220 is connected to the local network 254 through a network interface or adapter 256. In a networked environment, program modules depicted relative to the computing system 220, or portions thereof, may be stored in the remote memory storage device. It will be appreciated that the network connections shown are exemplary and other means of establishing a communications link between the computers may be used.

In certain embodiments, the fabrication device 270 includes a rapid prototyping machine configured to print wax patterns. Examples of such a rapid prototyping machine are the SLA® systems produced by 3D Systems of Rock Hill, S.C. However, any type of fabrication device 270 may be used without deviating from the spirit and scope of the disclosure. In certain embodiments, the fabrication device 270 can be connected to the computing system 220 via an appropriate interface 258. In a preferred embodiment, the fabrication device is configured to print the guide arrangement in surgical grade polymer. Although in other embodiments the fabrication device will print the guide arrangement in any material suitable for use as a dental guide arrangement.

The interface 258 can connected to the bus 230 such that the electronic model data may be retrieved from the appropriate or desired memory location. In some embodiments, the interface 258 converts the electronic models generated on the computing system 220 to a format readable by the fabrication device 270. In one example embodiment, the interface 258 converts the electronic model to an STL file. The converted file can be transmitted to the fabrication device 270 using a direct line connection or using a networked connection described above.

In certain embodiments, the design and production system 200 also includes a scanner 210 configured to implement the obtain operation 106 of the treatment process 100 of FIG. 2. For example, a three-dimensional scanner 210 can be coupled to the computing system 220 via an appropriate scanner interface 260. The scanner interface 260 is connected to the bus 230 such that the scanned data may be stored in the appropriate or desired memory location, manipulated by the CPU 222, displayed on the display device 246, etc. Preferred scanners include a laser line scanner arranged and configured for scanning line study casts (e.g., plaster casts), such as the dental scanner manufactured by GeoDigm Corporation of Minnesota. The operation and scanning methodology used by such a line scanner is generally described in U.S. Pat. No. 6,217,334. However, any suitable scanner 210 may be used and a number of other methodologies might be employed to generate the scanned image data.

Portions of the preferred embodiment constructed in accordance with the principles of the present disclosure utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The implementation is a matter of choice dependent on the performance requirements of the computing system implementing the disclosure. Accordingly, the logical operations making up the embodiments of the disclosure described herein can be variously referred to as operations, steps, or modules.

As just discussed in reference to FIG. 10, a system of the present disclosure may comprise a three-dimensional scanner configured to obtain spatial data corresponding to dentition of a patient, a computing system coupled to the three-dimensional scanner, the computing system configured to generate an electronic model image representing the dentition of the patient based on the spatial data obtained by the scanner, the computing system also configured to generate an electronic model image of an guide arrangement, the guide arrangement configured to define a desired gingival contour of the teeth; and a fabricating device coupled to the computing system, the fabricating device configured to fabricate the guide arrangement based on the electronic model images of the guide arrangement.

Figure 11:
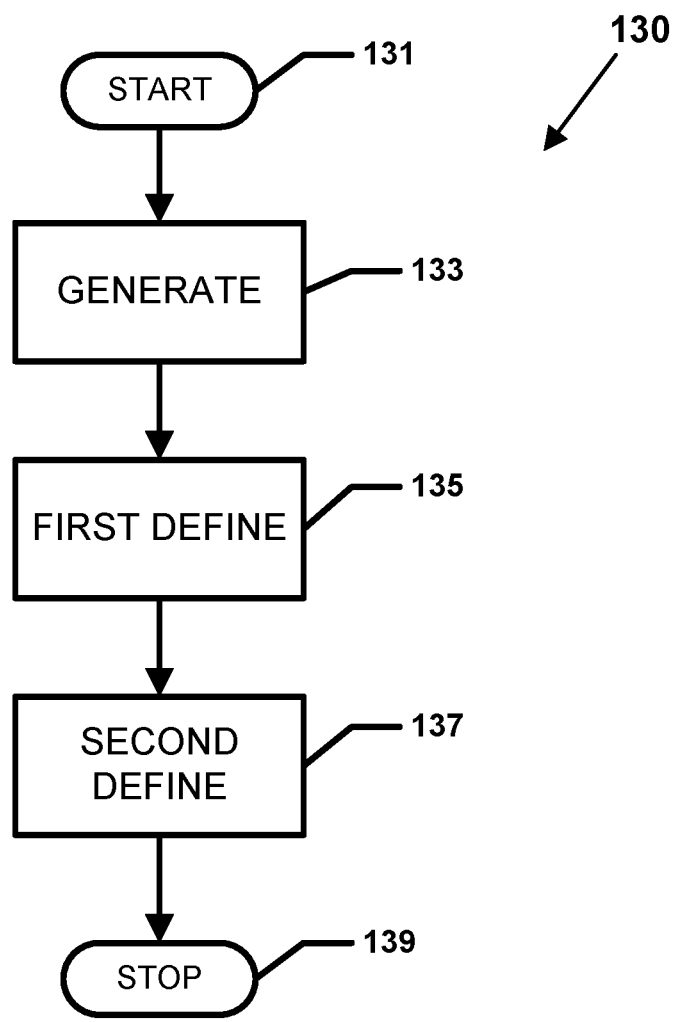
FIG. 11 is a flowchart illustrating an operational flow for a design process by which a guide arrangement model may be produced in accordance with aspects of the disclosure.

FIG. 11 is a flowchart illustrating an operational flow for a design process 130 by which a guide arrangement model 300 may be produced. For example, the design process 130 may be used to implement the design operation 114 of manufacturing process 110 of FIG. 9. The design process 130 begins at a start module 131, performs any appropriate initialization procedures, and proceeds to a generate operation 133 at which the guide model 300 is produced.

In some implementations, the generate operation 133 generates a standard electronic model having a default size and shape. In other implementations, the generate operation 133 generates the guide model 300 based on parameters (e.g., spatial data for the teeth, the gingival margin, etc.) obtained from the dentition model 30 or other spatial data. In some implementations, the generate operation 133 produces a guide model 300 sized and shaped to fit over a single tooth. In other implementations, the generate operation 133 produces a guide model 300 sized and shaped to fit over multiple adjacent teeth.

Figure 12:
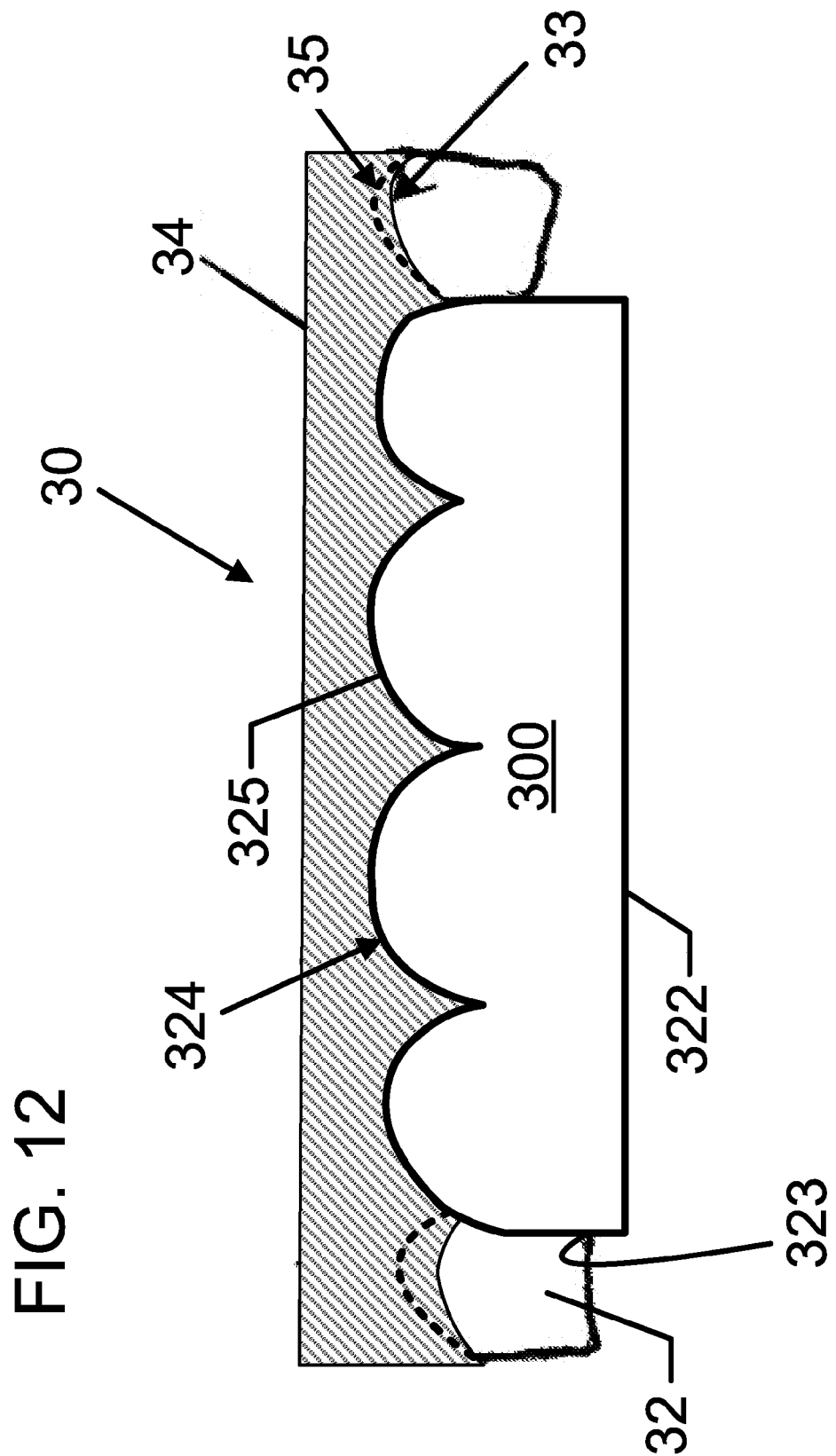
FIG. 12 is a front elevational view of an example guide model positioned over a dentition model so that a guide edge of the guide model follows the incision path.

A first define operation 135 defines or adjusts the outer boundaries of the guide model 300. In some implementations, the first define operation 135 creates the template portion 324 of the guide model 300 by creating a guide edge 325 along the contours of the incision path 35. For example, FIG. 12 is a front elevational view of an example guide model 300 positioned over a dentition model 30 so that a guide edge 325 of the guide model 300 follows the incision path 35.

Figure 13:
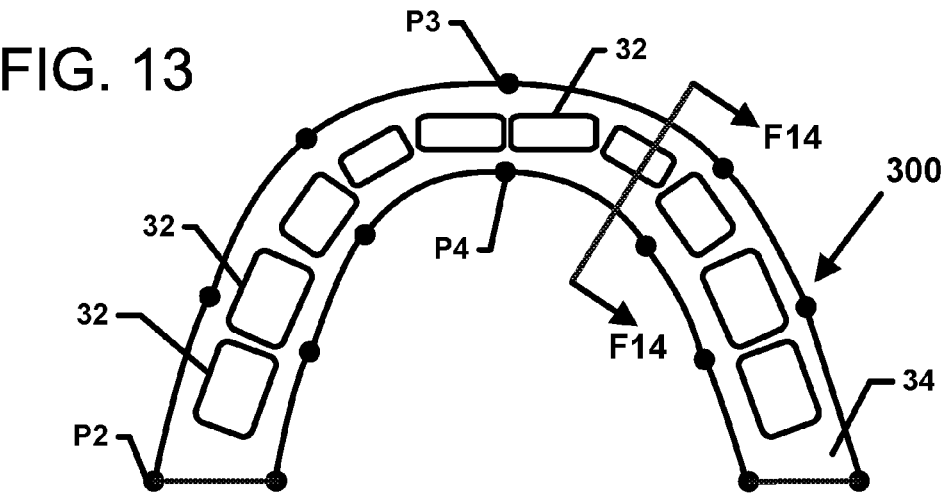
FIG. 13 is a plan view of a dentition model including teeth and gingiva and including outer boundaries for an example guide arrangement model that are defined by line segments connecting control points (e.g., points P1, P2, P3, etc)

In some implementations, the first define operation 135 enables a technician to interactively adjust the outer boundaries using control points. For example, FIG. 13 is a plan view of a dentition model 30 including teeth 32 and gingiva 4. Outer boundaries for the guide arrangement model 300 are defined by line segments connecting control points (e.g., points P1, P2, P3, etc). A technician can move one or more of the control points to different locations to adjust the distance between the buccal surface of the guide model 300 and the buccal surface of each tooth 32 and/or to adjust the distance between the lingual surface of the guide model 300 and the lingual surface of each tooth 32.

Figure 14:
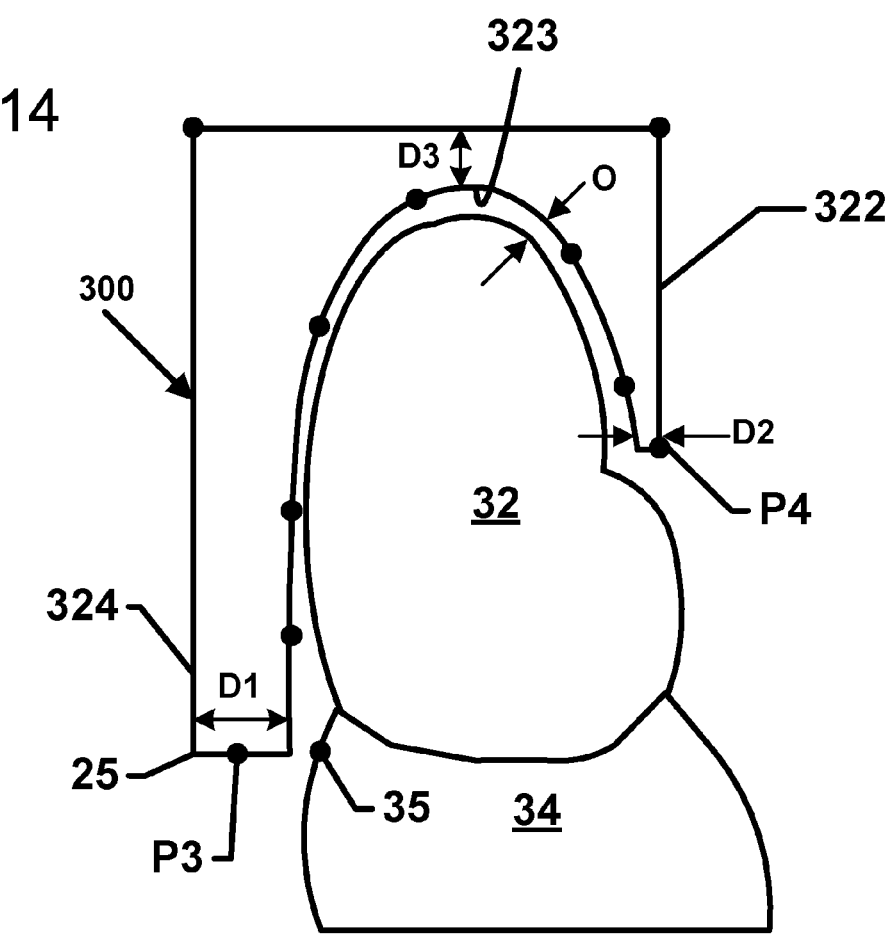
FIG. 14 shows a slice of the dentition model and guide model taken along the F14-F14 line of FIG. 13.

FIG. 14 shows a slice of the dentition model 30 and guide model 300 taken along the F14-F14 line of FIG. 13. As shown, a control point P3 on the guide edge 325 aligns with the incision path 35. In some implementations, in the first define operation 135, a technician may take one or more such slices along the dentition of FIG. 13 to view the interaction between the guide model 300 and the dentition model 30. At each slice, the positions of the control points may be adjusted. In certain implementations, positions of the control points, such as control point P3, are modified to better align with the incision path 35.

In other implementations, in the first define operation 135, the positions of the control points may be modified to increase or decrease a thickness of the guide model 300 at different locations along the surface of the tooth 32. For example, the control points my be manipulated to increase the thickness D1 of the template portion 324 of the guide model 300, the thickness D2 of the mounting portion 322 of the guide model 300, and/or the thickness D3 of the occlusal surface of the guide model 300.

A second define operation 137 creates the interface region 323 of the guide model 300 by defining the interior contours of the guide model 300. In some implementations, the interface region 323 of the guide model 300 is shaped to fit over at least the buccal side of the tooth 32. In certain implementations, the interface region 323 of the guide model 300 is configured to fit over the occlusal surface of the tooth 32. In certain implementations, the interface region 323 of the guide model 300 extends from the buccal side of the tooth 32, over the occlusal surface, to a lingual side of the tooth 32.

As shown in FIG. 14, in some implementations, one or more control points can be provided along the interface region 323 to enable a technician to interactively adjust the contours of the interface region 323. For example, the second define operation 137 may adjust the control points to increase or decrease on offset O defined between the interface region 323 and the tooth 32. In some implementations, the offset O is formed sufficiently large, for example, to accommodate adhesive to bond a fabricated guide arrangement 16 to a tooth 2 of the patient (see FIGS. 7-8). In other implementations, the offset O is formed sufficiently small, for example, to provide an interference fit (i.e., friction fit) between a fabricated guide arrangement 16 and the tooth 2 of the patient.

The design operation 130 performs any appropriate completion procedures and ends at a stop module 139.

FIG. 15 is a flowchart illustrating an operational flow for surgical process 190 using a fabricated guide arrangement 16. For example, the surgical process 190 may be used to at least partially execute the implement operation 108 of the treatment process 100 of FIG. 2. The surgical process 190 begins at a start module 191, performs any appropriate initialization procedures, and proceeds to a mount operation 193.

In a mount operation 193, a dental professional positions the guide arrangement 16 at an appropriate location in the patient's mouth. For example, as shown in FIG. 16, the guide arrangement 16 may be positioned over one or more teeth 2 of the patient. The template portion 24 extends towards the gingival surface 4 until the guide edge 25 aligns with a desired incision path 35. In other implementations, however, the guide arrangement 16 may be positioned over a fully or partially edentulous arch of the patient.

In some implementations, mounting of the guide arrangement 16 can be implemented using a friction-fit between the guide arrangement 16 and the teeth 32. For example, in some instances the friction is great enough to forego the use of any dental adhesive, gum, or glue. In other implementations, the guide arrangement 16 is mounted to the teeth 2 using an adhesive to maintain a fixed position while the dental professional cuts the gingiva 4 of the patient. In still other embodiments, the guide arrangement 16 is mounted to the teeth 2 by having the patient bite down on the guide arrangement 16. Further still, a dental professional can use all of some of the above described mounting methods.

Following mounting of the guide arrangement 16, a dental professional implements an align operation 195 in which a cutting tool 60 is positioned so that a cutting section 62 extends towards the gingiva 4 at a point along the incision path 35. In some implementations, the cutting tool 60 includes a scalpel, gingivectomy knife, or other such sharp. In some such implementations, the blade 62 or pointed tip that abuts the guide edge 25 of the guide arrangement 16. In other such implementations, a handle of the cutting tool 60 may abut the guide edge 25 of the guide arrangement 16. In still other implementations, the cutting tool 60 includes a laser that fits with the guide arrangement 16 to align the laser beam along the incision path 35.

In a cut operation 197, the dental professional makes one or more incisions into the gingiva 4 using the cutting section 62 of the cutting tool 60. In some implementations, the dental professional slides the cutting tool 60 along the guide edge 25 to trace a portion of the incision path. In other implementations, the dental professional slides the cutting tool 60 forwardly and rearwardly along the guide edge 25 at a point along the incision path 35. In still other implementations, the dental professional "eyeballs" the movements of the cutting tool 60 without any physical contact between the cutting tool 60 and the guide 16.

The surgical process 190 performs any appropriate completion procedures and ends at a stop module 199.

Figure 17:
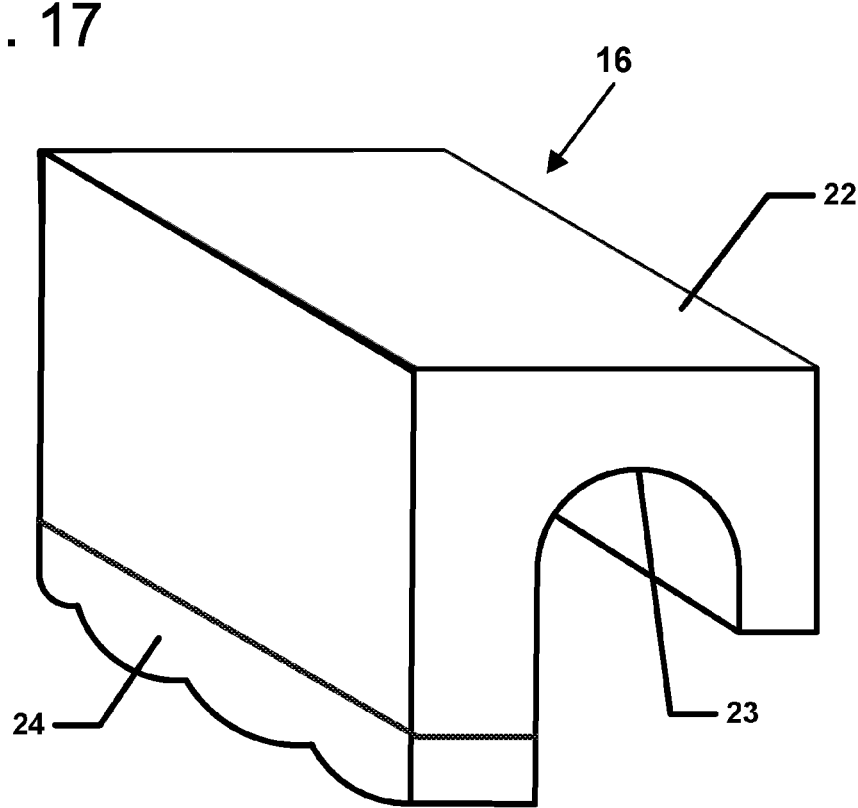
FIGS. 17 and 18 show another example implementation of a guide arrangement having a mounting portion and a template portion formed of different materials.
Figure 18:
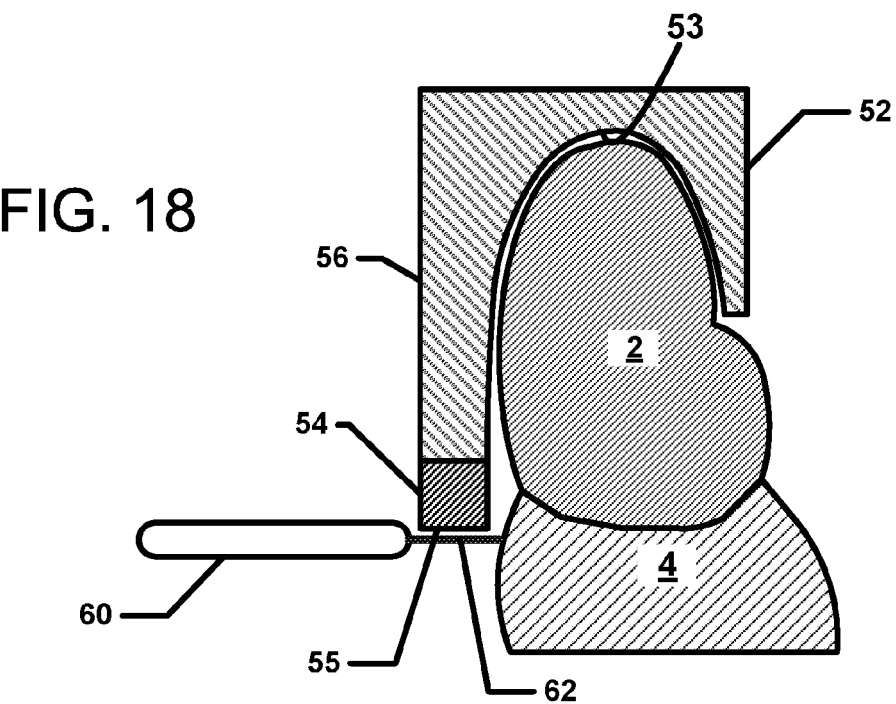

FIGS. 17 and 18 show another example implementation of a guide arrangement 50 having a body 51 including a mounting portion 52 and a template portion 54. The mounting portion 52 defines an interface region 53 that is substantially the same as interface region 23 of the first example guide arrangement 16. Various embodiments of the mounting portion 52 may extend over the buccal surface, occlusal surface, and/or lingual surface of one or more teeth 2. The template portion 54 defines a guide edge 55 that follows the contours of a planned incision path.

In this example implementation, however, the mounting portion 52 and template portion 54 may be formed from two different materials. For example, the template portion 54 may be formed of dental metal or other hard material to withstand interactions with the cutting section 62 of the cutting tool 60. The mounting portion 52 may be formed out of any biocompatible material (e.g., dental wax, metal, etc.). In certain implementations, the material forming the mounting portion 52 need not be as strong or rigid as the material forming the template portion 54.

In some implementations, electronic models of the mounting portion 52 and the template portion 54 are designed to fit together in a single guide model (e.g., model 300 of FIG. 12). In certain implementations, the mounting portion 52 and the template portion 54 may be fabricated separately and subsequently attached together (e.g., using adhesive, welding, or other such fastening techniques). For example, the fabricated template portion 54 may be attached to a buccal section 56 of the mounting portion 52.

In other implementations, the template portion 54 may be cast or milled first and the mounting portion 52 may be cast around the template portion 54. For example, in one implementation, the fabricated template portion 54 may be attached to a pattern of the mounting portion to form a casting assembly. The casting assembly is invested, the pattern is destroyed, and material forming the mounting portion 52 is poured into the mold to fuse to the template portion 54.

Figure 19:
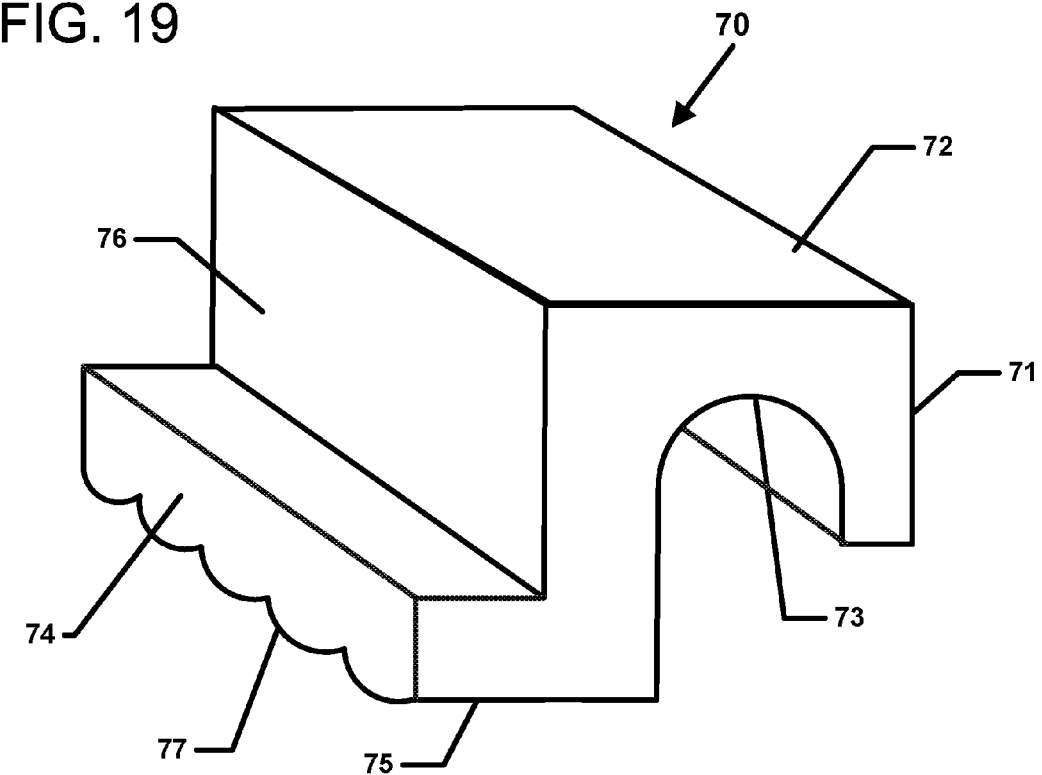
FIGS. 19 and 20 show another example implementation of a guide arrangement including a stopping lip formed by a protrusion from a buccal side of the guide arrangement.
Figure 20:
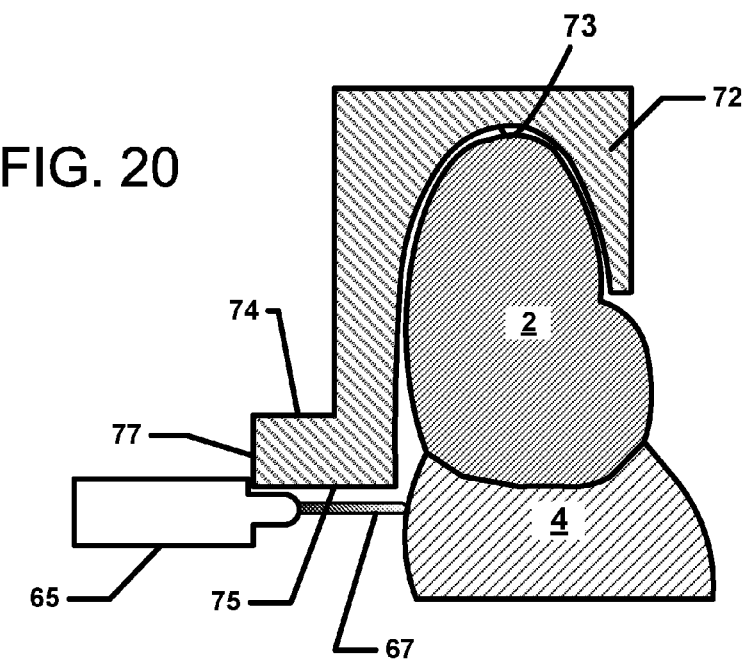

FIGS. 19 and 20 show another example implementation of a guide arrangement 70 having a body 71 including a mounting portion 72 and a template portion 74. The mounting portion 72 defines an interface region 73 that is substantially the same as interface region 23 of the first example guide arrangement 16. Various embodiments of the mounting portion 72 may extend over the buccal surface, occlusal surface, and/or lingual surface of one or more teeth 2. The template portion 74 defines a guide edge 75 that follows the contours of a planned incision path. As noted above, the mounting portion 72 and the template portion 74 may be formed of different material.

Figure 21:
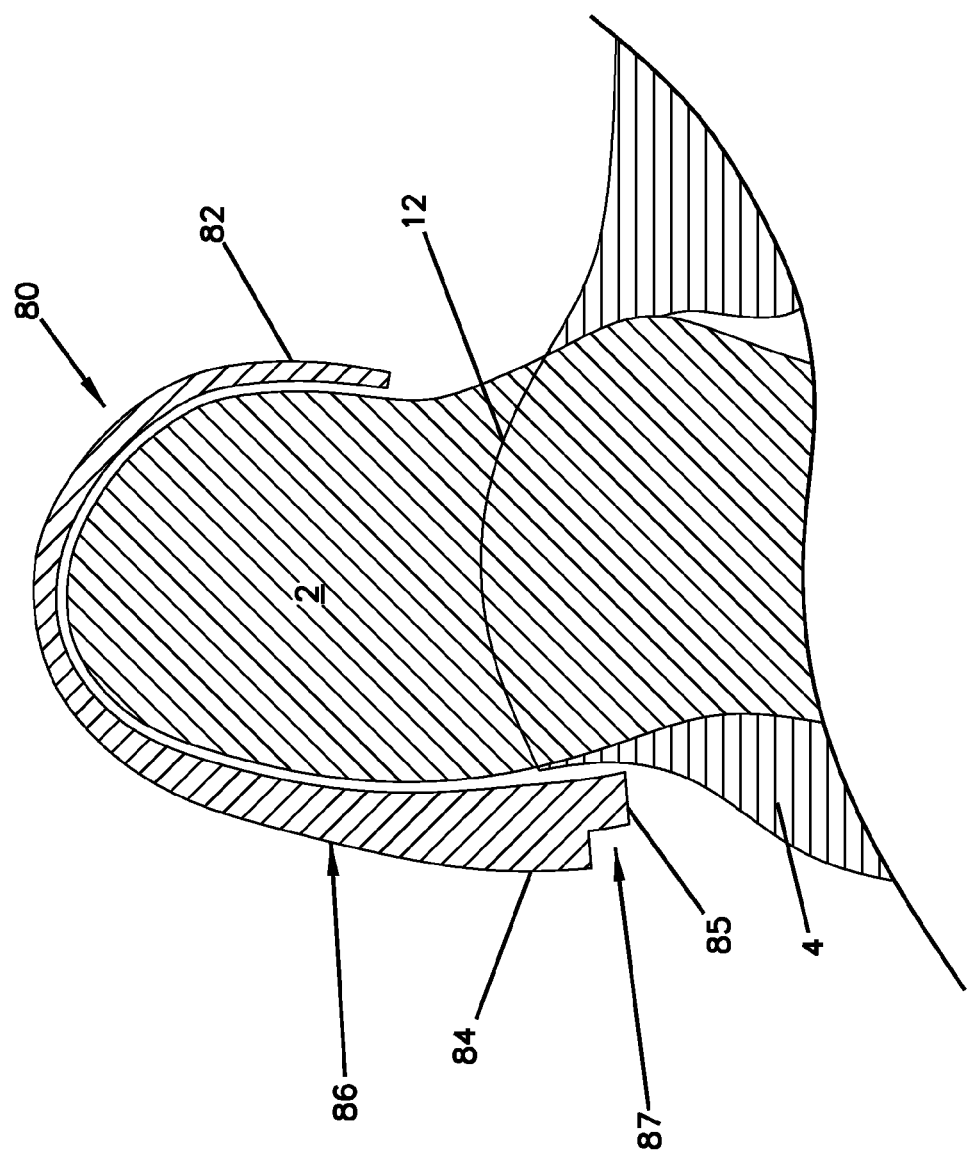
FIG. 21 shows another example implementation of a guide arrangement having a stopping lip formed by a notch in the template portion of the guide arrangement.

The guide arrangement 70 also includes a stopping lip 77 at the buccal side 76 of the guide arrangement 70. The stopping lip 77 is sized, shaped, and positioned to limit the proximity of a cutting tool 65 to the gingival surface 4 of the patient. In some implementations, the stopping lip 77 protrudes from the buccal side 76 of the guide arrangement 70. In other implementations, the stopping lip 77 is defined by a notch 87 in the buccal side 86 of the guide arrangement 80 (see FIG. 21, showing an embodiment including the guide arrangement 80, the mounting portion 82, the template portion 84, the guide edge 85, the buccal side 86, and the notch 87, as well as a tooth 2, the gingeva 4, and the gingival margin 12.). In certain implementations, the stopping lip 77 has an edge formed from metal, a dental grade material resistant to cutting, or a material providing reduced friction to facilitate movement of the cutting tool 65 along the guide edge 75.

In some implementations, the stopping lip 77 facilitates using a dental laser as the cutting tool 65. For example, the laser 65 may be positioned so that a portion of the laser body abuts the stopping lip 77. While resting against the stopping lip 77, the dental laser is maintained at the optimal distance from the gingiva 4 to cut the gingiva 4 safely.

In certain implementations, the cutting tool 65 is abutted to a stopping lip 77 on the template portion 74 of the guide arrangement 70 to limit the proximity of the cutting tool 65 to the gingival surface 4. In some implementations, the stopping lip 77 limits the distance between the cutting tool 65 and the gingival surface 4 to a range of about 0.01 mm to about 2.0 mm. Indeed, in some implementations, the stopping lip 77 limits the distance to a range of about 0.15 mm to about 1.8 mm. In certain implementations, the stopping lip 77 limits the distance to between about 0.2 mm and about 1.6 mm. In certain implementations, the stopping lip 77 limits the distance to between about 0.25 mm and about 1.4 mm. In certain implementations, the stopping lip 77 limits the distance to between about 0.3 mm and about 1.2 mm. In certain implementations, the stopping lip 77 limits the distance to between about 0.35 mm and about 1.0 mm. In certain implementations, the stopping lip 77 limits the distance to between about 0.4 mm and about 0.8 mm. In one implementation, the stopping lip 77 limits the distance to between about 0.45 mm and about 0.6 mm. In one implementation, the stopping lip 77 limits the distance to between about 0.45 mm and about 0.55 mm.

Although embodiments of the present disclosure have been described with respect to digitizing a dental cast of a patient, it should be appreciated that the principles of the present disclosure can also be applied to a digitized impression or a direct scan of the dentition of a patient. In the former case, a computer can invert the scanned impression to provide a positive image of the patient's teeth.

The foregoing description of the exemplary embodiments of the disclosure has been presented for the purposes of illustration and description. They are not intended to be exhaustive or to limit the disclosure to the precise forms disclosed. Many modifications and variations are possible in light of the above teaching. It is intended that the scope of the disclosure be limited not with this detailed description, but rather by the claims appended hereto.

What is claimed is:

1. A gum tissue modification guide arrangement for modifying gum tissue of a patient, the guide arrangement comprising:
 a mounting portion defining an interface configured to seat on one or more teeth of the patient; and
 a template portion coupled to the mounting portion and comprising a contoured guide edge disposed along a gingival surface on a buccal side of the guide arrangement, wherein the contoured guide edge defines a desired incision path for modifying gum tissue on the buccal side of the one or more teeth and provides a surface along which a cutting tool may be positioned and moved to cut the gum tissue, wherein the contoured guide edge is shaped according to an electronic model designed by a computer system defining the desired incision path, and wherein the contoured guide edge is configured to extend beyond a gingival margin of the patient when the mounting portion is coupled to the one or more teeth of the patient.

2. The guide arrangement of claim 1, wherein the mounting portion and the template portion are fabricated as a single arrangement.

3. The guide arrangement of claim 1, wherein the mounting portion couples to the buccal surface of the dentition of the patient.

4. The guide arrangement of claim 1, wherein the mounting portion couples to at least the buccal and occlusal surfaces of the dentition of the patient.

5. The guide arrangement of claim 1, wherein the dentition of the patient includes between two and 16 teeth.

6. The guide arrangement of claim 1, further comprising a safety lip along the template portion of the guide arrangement.

7. The guide arrangement of claim 6, wherein the safety lip is positioned to limit the proximity of a cutting tool to the gingival surface.

8. The guide arrangement of claim 1, wherein the arrangement is fabricated from surgical grade polymer.

* * * * *